United States Patent [19]
Long et al.

[11] Patent Number: 5,849,020
[45] Date of Patent: Dec. 15, 1998

[54] INDUCTIVELY COUPLED ELECTROSURGICAL INSTRUMENT

[75] Inventors: Gary L. Long, Cincinnati, Ohio; Lynetta J. Freeman, West Chester, Ohio; Bryan D. Knodel, Cincinnati, Ohio

[73] Assignee: Ethicon Endo-Surgery, Inc., Cincinnati, Ohio

[21] Appl. No.: 885,517

[22] Filed: Jun. 30, 1997

[51] Int. Cl.[6] ................................................. A61B 17/32
[52] U.S. Cl. ............................................. 606/167; 606/40
[58] Field of Search ................................. 606/167, 170, 606/169, 40, 38, 32, 28, 185

[56] References Cited

U.S. PATENT DOCUMENTS

| | | |
|---|---|---|
| 1,620,929 | 3/1927 | Wallerich . |
| 4,535,773 | 8/1985 | Yoon ........................................ 604/51 |
| 4,674,010 | 6/1987 | Van Den Steen ........................ 361/433 |
| 4,717,438 | 1/1988 | Benge et al. ............................ 156/152 |
| 4,799,480 | 1/1989 | Abraham et al. ................... 128/303.13 |
| 4,825,217 | 4/1989 | Choi ........................................ 343/135 |
| 4,884,982 | 12/1989 | Fleming et al. ........................ 439/620 |
| 4,934,960 | 6/1990 | Capp et al. ............................. 439/620 |
| 4,936,842 | 6/1990 | D'Amelio et al. ......................... 606/42 |
| 5,105,829 | 4/1992 | Fabian et al. ............................ 128/899 |
| 5,124,509 | 6/1992 | Hoendervoogt et al. ................. 178/19 |
| 5,207,691 | 5/1993 | Nardella ................................. 606/142 |
| 5,273,524 | 12/1993 | Fox et al. ................................. 604/21 |
| 5,342,356 | 8/1994 | Ellman et al. ............................ 606/32 |
| 5,342,357 | 8/1994 | Ellman et al. ............................ 606/32 |
| 5,344,420 | 9/1994 | Hilal et al. ............................... 606/28 |
| 5,380,321 | 1/1995 | Yoon ........................................ 606/41 |
| 5,383,860 | 1/1995 | Lau ........................................ 604/167 |
| 5,387,196 | 2/1995 | Green et al. ............................ 604/164 |
| 5,387,197 | 2/1995 | Smith et al. ............................ 604/164 |
| 5,391,166 | 2/1995 | Eggers ...................................... 606/48 |
| 5,403,312 | 4/1995 | Yates et al. ............................... 606/48 |
| 5,417,687 | 5/1995 | Nardella et al. .......................... 606/32 |
| 5,432,486 | 7/1995 | Wong ...................................... 333/109 |
| 5,437,277 | 8/1995 | Dumoulin et al. .................... 128/652.1 |
| 5,443,462 | 8/1995 | Hannant .................................. 606/34 |
| 5,445,142 | 8/1995 | Hassler, Jr. ............................. 600/105 |
| 5,445,638 | 8/1995 | Rydell et al. ............................ 606/51 |
| 5,540,684 | 7/1996 | Hassler, Jr. ............................. 606/40 |
| 5,545,142 | 8/1996 | Stephens et al. ....................... 604/167 |
| 5,562,611 | 10/1996 | Transue ................................... 604/26 |
| 5,591,192 | 1/1997 | Privitera et al. ....................... 606/185 |
| 5,597,107 | 1/1997 | Knodel et al. ....................... 227/175.2 |
| 5,733,323 | 3/1998 | Buck et al. ............................. 607/122 |

Primary Examiner—Michael Buiz
Assistant Examiner—Kevin Truong
Attorney, Agent, or Firm—Bernard E. Shay

[57] ABSTRACT

In the present invention, a cordless inductively coupled electrosurgical instrument is adapted to receive electrosurgical energy from a specially designed trocar or trocar adapter. In one embodiment of the present invention, an electrosurgical instrument includes a handle, an elongated tube and an electrosurgical end effector. The handle may include an actuator such as a trigger which is operatively connected to the end effector through the elongated tube. The elongated tube may be, for example, a closure tube which is adapted to close the end effector when the handle actuator is moved. The electrosurgical end effector is adapted to apply electrosurgical energy to biological tissue in order to effect treatment of the tissue. The elongated closure tube includes one or more inductor coils adapted to couple electrosurgical energy to the end effector. The one or more inductor coils are electrically connected to the end effector through one or more electrical conductors.

18 Claims, 11 Drawing Sheets

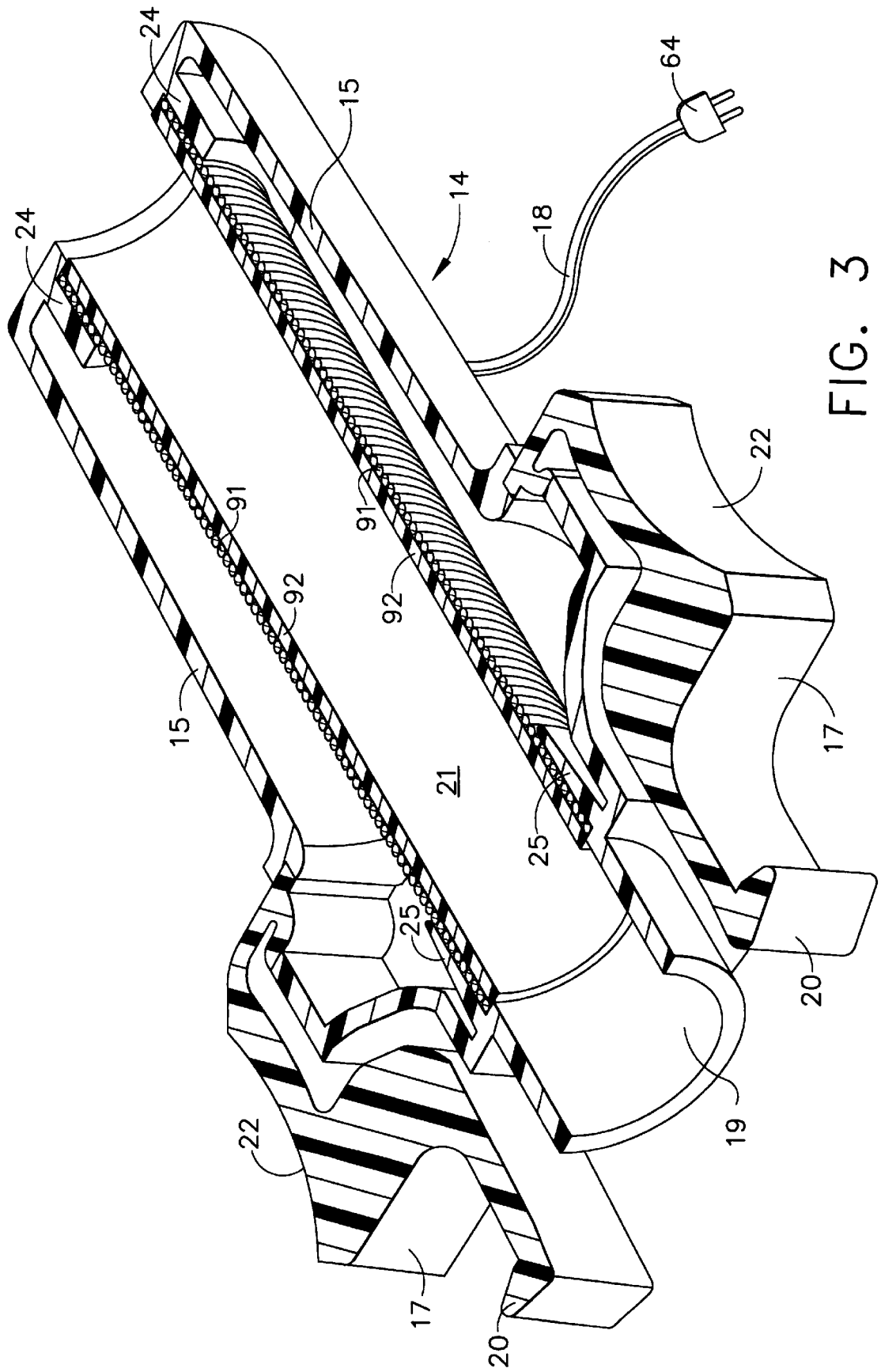

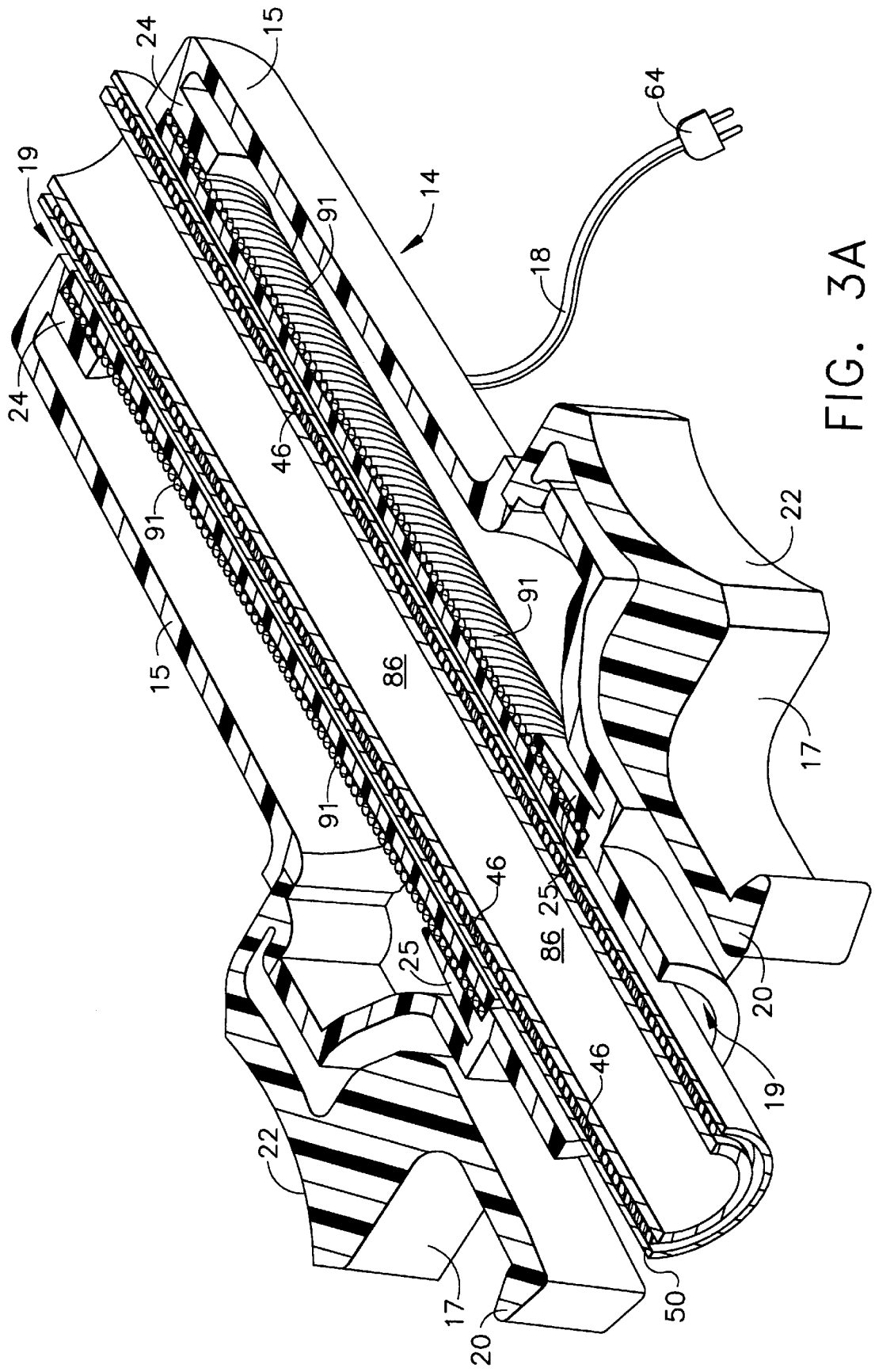

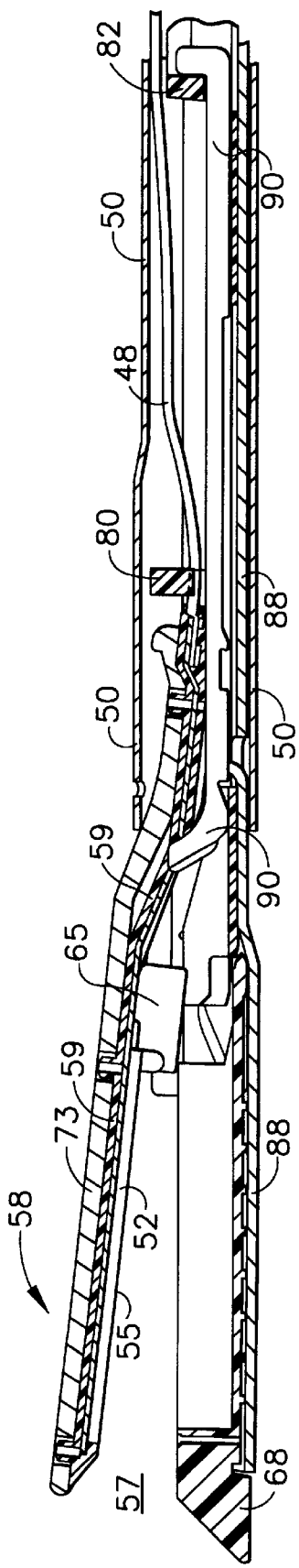
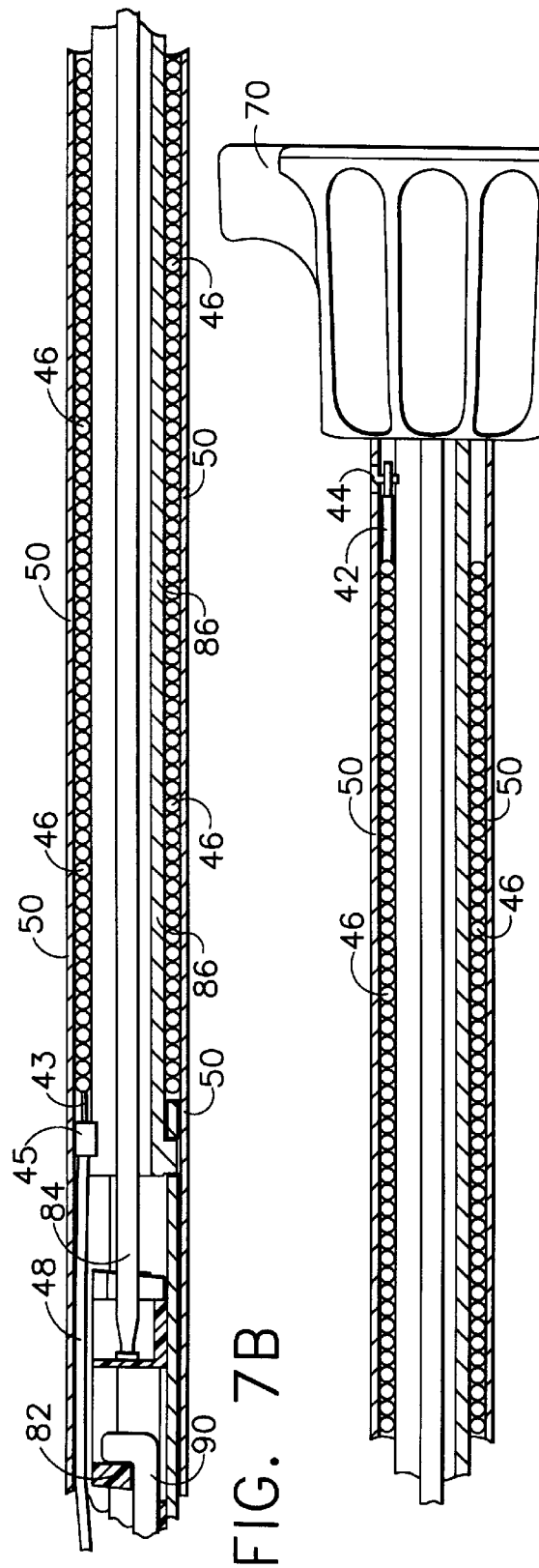
FIG. 7A
FIG. 7B
FIG. 7C

INDUCTIVELY COUPLED ELECTROSURGICAL INSTRUMENT

This application is related to the following copending applications: application Ser. No. 08/856,534 filed May 14, 1997; application Ser. No. 08/877,715, filed Jun. 18, 1997; application Ser. No. 08/878,421, filed Jun. 18, 1997; application Ser. No. 08/885,458, filed Jun. 30, 1997; application Ser. No. 08/884,949, filed Jun. 30, 1997; and application Ser. No. 08/885,166, filed Jun. 30, 1997, which applications are hereby incorporated herein by reference.

FIELD OF THE INVENTION

The present invention relates, in general, to an improved electrosurgical instrument and method of use and, more particularly, to an inductively coupled cordless electrosurgical instrument adapted to receive electrosurgical energy from a specially adapted electrosurgical trocar.

BACKGROUND OF THE INVENTION

The surgical trocar has become the mainstay in the development and acceptance of endoscopic surgical procedures. Endoscopic surgery involves the performance of surgery through a number of openings having a relatively small diameter. These openings are made with the trocar, which typically includes a trocar obturator and a trocar cannula. The obturator is the piercing implement which punctures the body wall to make the opening. Once the puncture is made, the obturator is withdrawn from the cannula. The cannula then provides a small diameter passageway into and through the body wall to provide access for additional surgical instrumentation to the surgical site. The function, structure and operation of a typical trocar is described in detail in U.S. Pat. No. 5,387,197, which is hereby incorporated herein by reference.

Such additional surgical instruments may include, for example, bipolar or monopolar electrosurgical instruments which utilize radio frequency electrosurgical energy. Known electrosurgical instruments include, for example, bipolar forceps, bipolar scissors, monopolar-hooks, monopolar-scissors and bipolar endocutters. Each of those instruments has an electrosurgical end effector which is adapted to treat tissue through the application of electrosurgical (e.g. radio frequency or RF) energy to tissue which is brought in contact with the electrosurgical end effector. Most known electrosurgical instruments are connected by electrical cords to electrosurgical generators. The structure and operation of a typical mechanical cutter/stapler is described in U.S. Pat. No. 5,597,107 which is hereby incorporated herein by reference. The structure and operation of a typical bipolar cutter/stapler ("bipolar endocutter") is described in U.S. Pat. No. 5,403,312 which is hereby incorporated herein by reference.

Electrosurgical generators, such as the Force II generator (which is available from Valleylab of Bolder Colo.), supply electrical energy to known electrosurgical instruments through electrical cords. The electrical cords, being attached directly to the electrosurgical instrument, may make the electrosurgical instrument inconvenient to use. Alternatively, electrical cords may cause undesirable delays as one electrosurgical instrument is unplugged from the generator and another is plugged in. Thus, it would be advantageous to design a cordless electrosurgical instrument such as a cordless instrument wherein electrosurgical energy is inductively coupled to the instrument. However, such a cordless electrosurgical instrument would have to be connected to the electrosurgical generator through some alternate arrangement. Therefore, it would also be advantageous to design a trocar or a trocar adapter which is adapted to inductively couple electrosurgical energy to specially designed cordless electrosurgical instruments. It would further be advantageous to design a cordless electrosurgical instrument and electrosurgical trocar or trocar adapter wherein the electrosurgical energy is inductively coupled from the electrosurgical trocar to the cordless electrosurgical instrument when electrosurgical energy is applied to the electrosurgical trocar or trocar adapter.

SUMMARY OF THE INVENTION

In the present invention, a cordless inductively coupled electrosurgical instrument is adapted to receive electrosurgical energy from a specially designed trocar or trocar adapter. In one embodiment of the present invention, an electrosurgical instrument includes a handle, an elongated tube and an electrosurgical end effector. The handle may include an actuator, such as a trigger, which is operatively connected to the end effector through the elongated tube. The elongated tube may be, for example, a closure tube which is adapted to close the end effector when the handle actuator is moved. Alternatively, the closure tube may include a mechanism connecting the handle actuator to the end effector, which mechanism acts to close the end effector when the handle actuator is moved. The electrosurgical end effector is adapted to apply electrosurgical energy to biological tissue in order to effect treatment of the tissue. The elongated closure tube includes one or more inductor coils adapted to couple electrosurgical energy to the end effector. The one or more inductor coils are electrically connected to the end effector through, for example, one or more electrical conductors.

In one embodiment of the present invention, the elongated closure tube is electrically conductive and is electrically connected to one end of the inductor coils and to one of the electrodes on the end effector. The opposite end of the inductor coil is connected to the opposing electrode on the end effector such that, when the end effector is used to grasp electrically conductive material (e.g. biological tissue), the electric circuit within the instrument is complete and electrical current can flow through the inductor coil and the biological tissue. In a further embodiment of the invention, the closure tube may be covered by an electrically insulating material.

In a further embodiment of the present invention, the electrosurgical instrument according to the present invention is adapted to fit through a trocar which includes an electrosurgical adapter. The electrosurgical adapter includes an elongated aperture with one or more inductor coils positioned around the aperture of the adapter and extending axially along the elongated aperture, at least a first electrical conductor, an outer housing and an electrical cord connected to the first conductor.

In a further embodiment of the present invention, the closure tube of the inductively coupled electrosurgical instrument is constructed, at least in part, of a ferromagnetic material, which may be, for example, iron. The adapter wall may alternatively be constructed of any material having a high relative magnetic permeability, that is, a permeability of greater than 100.

BRIEF DESCRIPTION OF THE DRAWINGS

The novel features of the invention are set forth with particularity in the appended claims. The invention itself, however, both as to organization and methods of operation, together with further objects and advantages thereof, may best be understood by reference to the following description, taken in conjunction with the accompanying drawings in which:

FIG. 3 is a perspective view in plane section of inductive electrosurgical adapter illustrated in FIG. 1.

FIG. 3A is a perspective view in plane section of the inductive electrosurgical adapter and closure tube illustrated in FIG. 1A.

FIG. 7A is a cutaway view of the end effector of the inductive electrosurgical instrument illustrated in FIG. 4.

FIG. 7B is a cutaway view of a central portion of the closure tube of the inductive electrosurgical instrument illustrated in FIG. 4.

FIG. 7C is a cutaway view of a proximal portion of the the closure tube of the inductive electrosurgical instrument illustrated in FIG. 4.

DETAILED DESCRIPTION OF THE INVENTION

Figure 1:
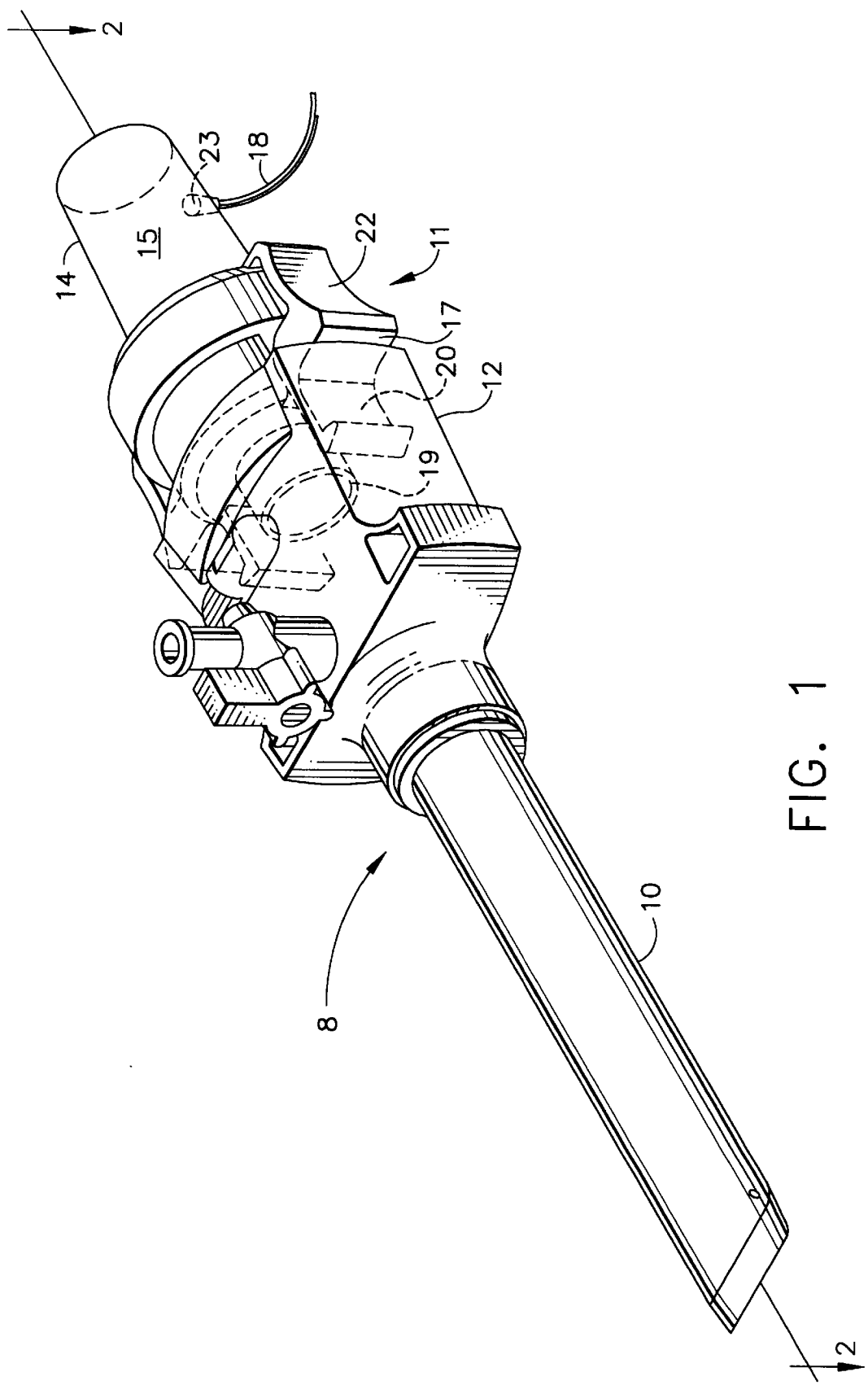
FIG. 1 is a perspective view of an inductive electrosurgical trocar according to the present invention.
Figure 1A:
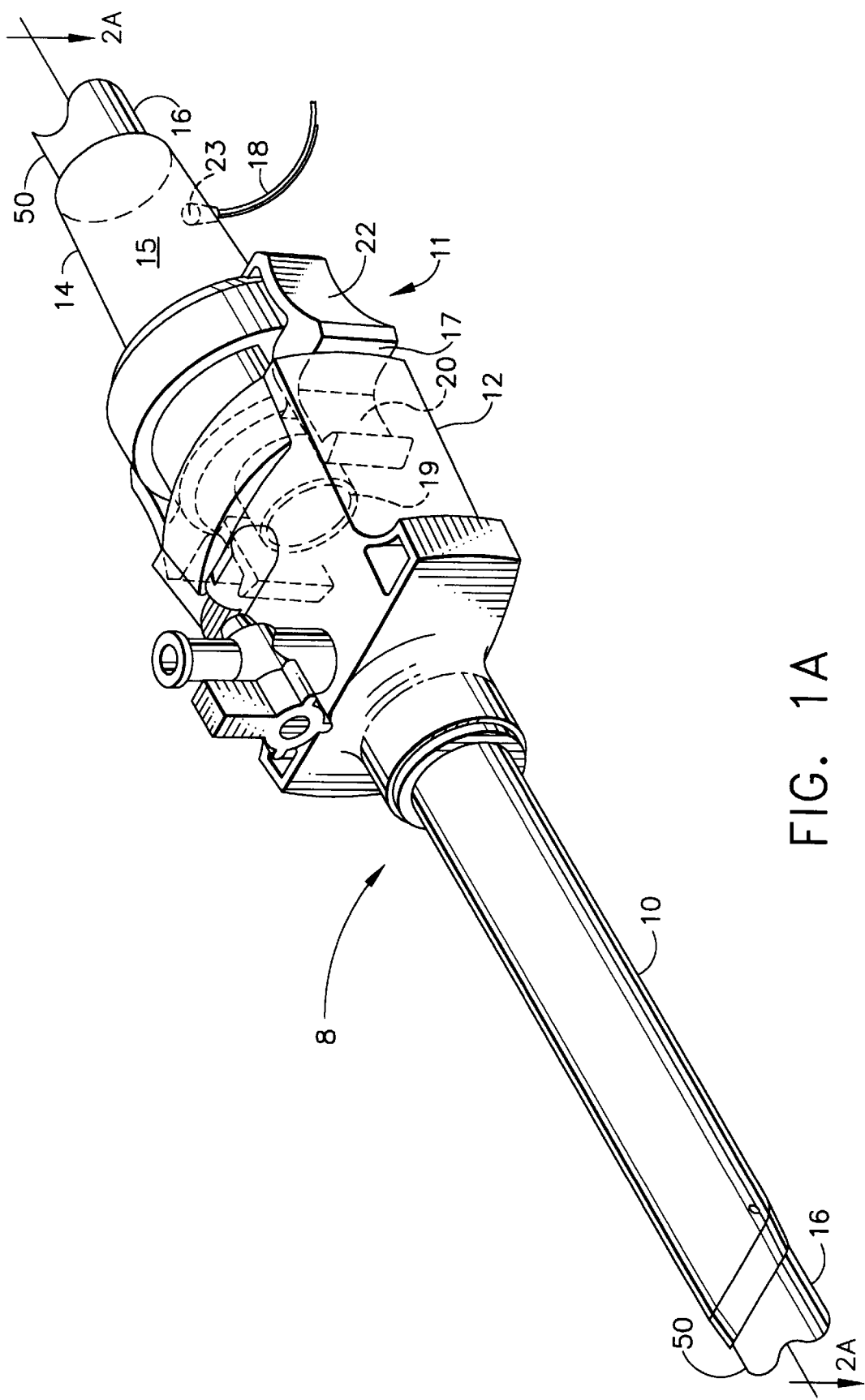
FIG. 1A is a perspective view of an inductive electrosurgical trocar including a portion of the closure tube of an inductive electrosurgical instrument according to the present invention wherein the closure tube is shown positioned in the central aperture of the inductive electrosurgical trocar.

FIG. 1 is a perspective view of an inductive electrosurgical trocar 11. FIG. 1A is a perspective view of inductive electrosurgical trocar 11 including a portion of closure tube 50 of inductive electrosurgical instrument 16 according to the present invention. Inductive electrosurgical trocar 11 includes trocar cannula 8 and a inductive electrosurgical adapter 14. Inductive electrosurgical trocar 11 may also include an obturator assembly (not shown) such as the one illustrated in U.S. Pat. No. 5,387,197, which has been previously incorporated herein by reference. Trocar cannula 8 includes cannula housing 12 and cannula tube 10, extending from cannula housing 12. Inductive electrosurgical adapter 14 includes an adapter housing 15, locking connector 17, central aperture 19, strain relief 23 and an electric cord 18. Inductive electrosurgical adapter 14 is connected to trocar cannula 8 by locking connector 17. Locking connector 17 includes locking cleats 20 and release buttons 22. It will be apparent that inductive electrosurgical adapter 14 may be integrated directly into trocar cannula housing 12, thus eliminating the need for locking connector 17.

Figure 2:
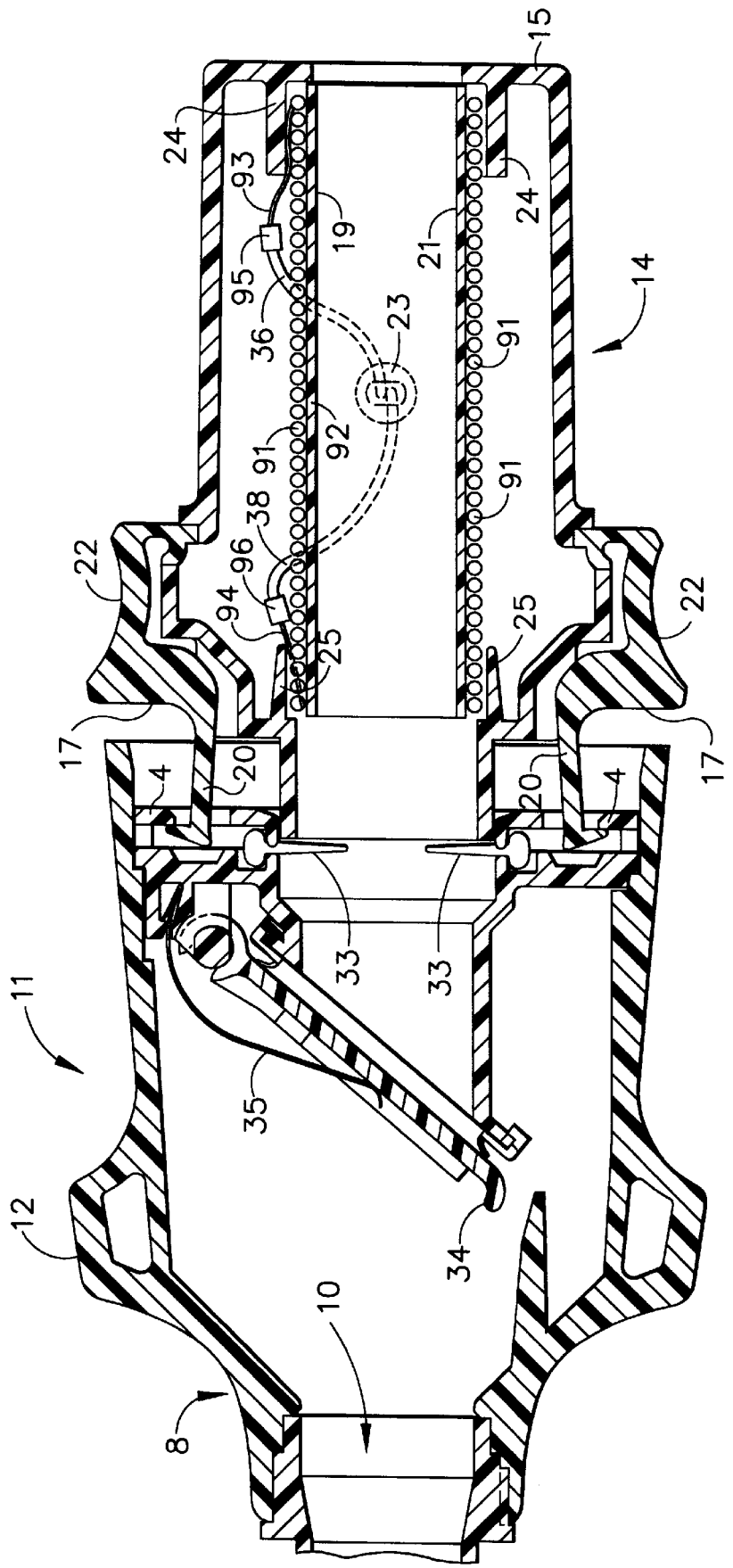
FIG. 2 is a plan view section taken along 2—2 in FIG. 1 through the proximal end of the inductive electrosurgical trocar illustrated in FIG. 1.
Figure 2A:
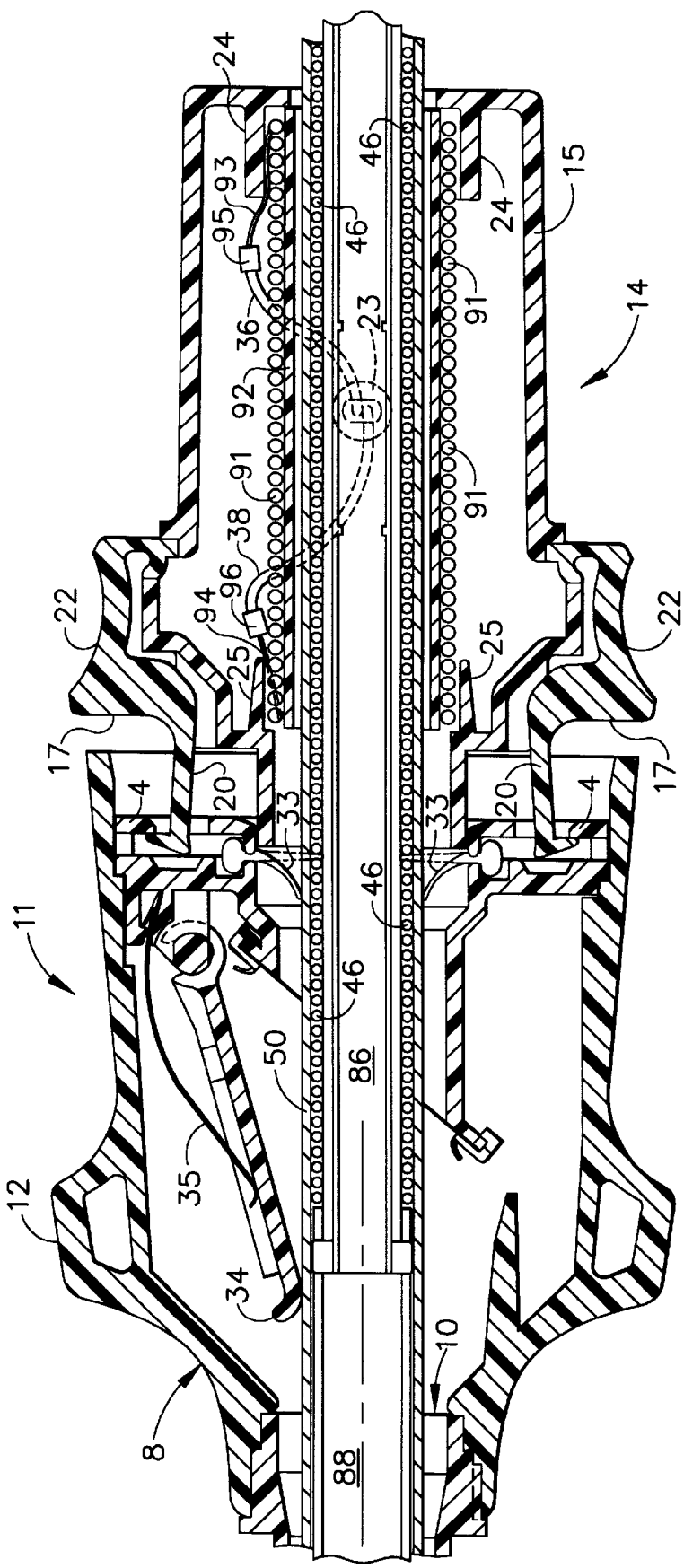
FIG. 2A is a plan view section taken along 2A—2A in FIG. 1A through the proximal end of the inductive electrosurgical trocar and closure tube illustrated in FIG. 1A.

FIG. 2 is a plan view section taken along 2—2 in FIG. 1 of the proximal end of inductive electrosurgical trocar 11. FIG. 2A is a plan view section taken along 2A—2A in FIG. 1A of the proximal end of inductive electrosurgical trocar 11 and a portion of closure tube 50 of inductive electrosurgical instrument 16. In FIGS. 2 and 2A, cannula housing 12 includes flapper valve 34, valve spring 35 and ring gasket 33. Inductive electrosurgical adapter 14 includes central aperture 19, front flange 25 and base flange 24. Central aperture 19 is an elongated aperture for receiving working instruments such as endoscopic electrosurgical instruments. Inductive electrosurgical adapter 14 further includes an inductor which, in the embodiment illustrated in FIGS. 2–3, comprises inductor coil 91, proximal inductor lead 93 and distal inductor lead 94. At least a portion of the wall of central aperture 19 is formed by interior wall 92 which may be formed of, for example, an insulating material to insulate inductor coil 91 from central aperture 19. Alternatively, interior wall 92 may be formed of, for example, a ferromagnetic material such as, for example, iron. Interior wall 92 is positioned against and held in place by front flange 25 and base flange 24. A compression member (not shown) such as, for example, an o-ring, may be positioned around interior wall 92 to bias interior wall 92 toward the center of central aperture 19. As illustrated in FIGS. 1, 1A, 2 and 2A, Electric cord 18 passes through strain relief 23 and is mechanically and electrically connected to upper conductor 36 and lower conductor 38. Upper conductor 36 is electrically connected to proximal inductor lead 93 by proximal connector 95. Proximal inductor lead 93 is electrically connected to the proximal end of inductor coil 91. Lower conductor 38 is electrically connected to distal inductor lead 94 by distal connector 96. Distal inductor lead 94 is electrically connected to the distal end of inductor coil 91. The portion of inductive electrosurgical instrument 16 illustrated in FIG. 2A includes closure tube 50, instrument inductor coil 46, channel retainer 86 and cartridge channel 88. Latch detents 4 in cannula housing 12, are adapted to receive locking cleats 20 of locking connector 17.

FIG. 3 is a perspective view in plane section of inductive electrosurgical adapter 14. FIG. 3A is a perspective view in plane section of inductive electrosurgical adapter 14 and a portion of closure tube 50 of inductive electrosurgical instrument 16. Referring now to FIGS. 2–3 and 2A–3A and particularly to FIGS. 3 and 3A, inductive electrosurgical adapter 14 includes adapter housing 15, locking cleats 20, central aperture 19, inductor coil 91, locking connector 17, interior wall 92, aperture interior surface 21, base flange 24, front flange 25 and release buttons 22. Electrosurgical energy is supplied to inductive electrosurgical adapter 14 by electric cord 18 which is connected to bipolar electrosurgical plug 64. Thus, electrosurgical energy may be coupled from bipolar electrosurgical plug 64 through electric cord 18 to inductor coil 91. Central aperture 19 is defined by aperture interior surface 21. The portion of aperture interior surface 21 visible in FIGS. 2, 2A, 3 and 3A is formed, at least in part, by the interior surface of interior wall 92. Strain relief 23 protects electric cord 18 as it passes through adapter housing 15.

Figure 4:
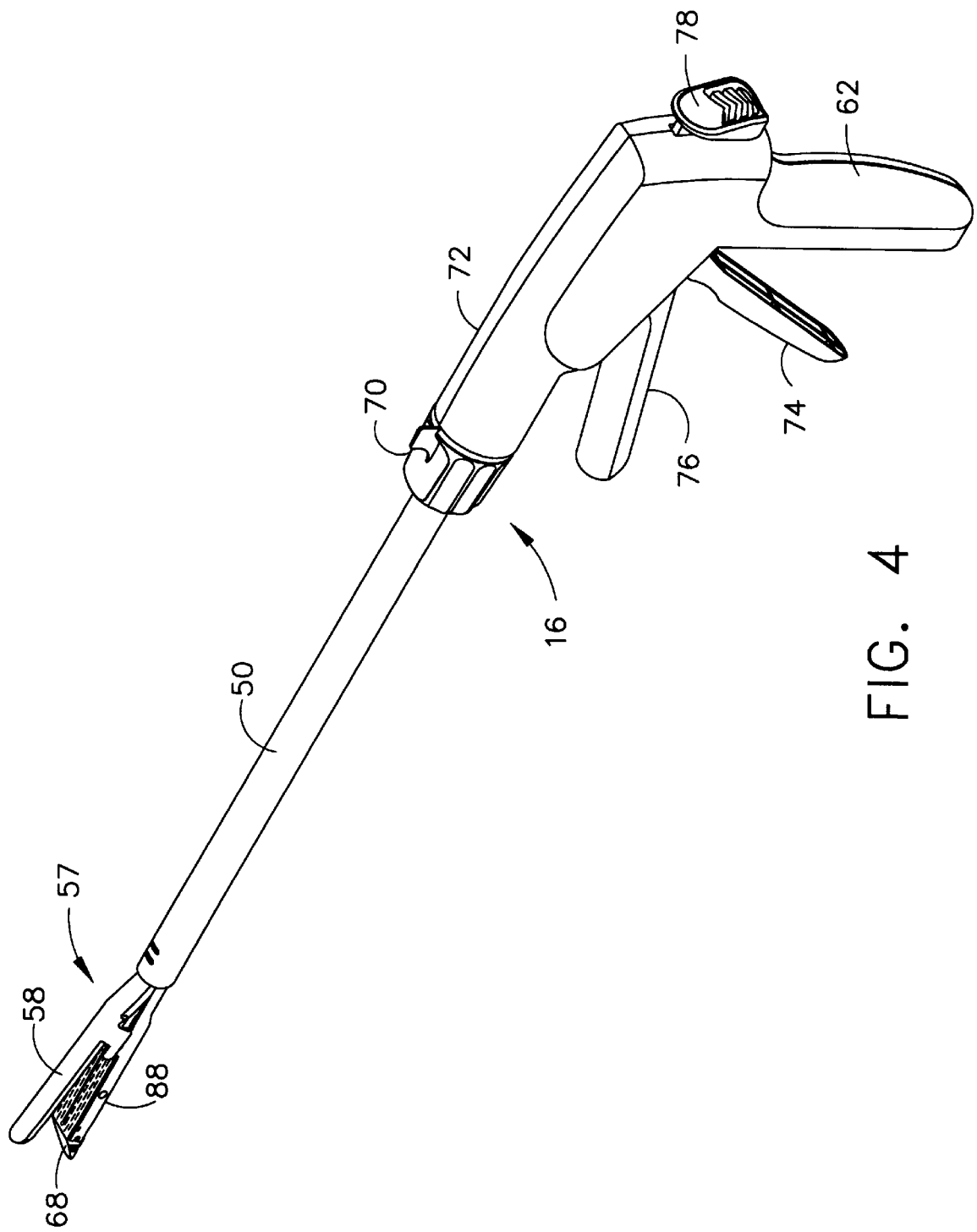
FIG. 4 is a perspective view of a cordless inductive electrosurgical instrument according to the present invention.

FIG. 4 is a perspective view of a inductive cordless electrosurgical instrument 16 which may be, for example, a bipolar cutter/stapler. In FIG. 4, inductive electrosurgical instrument 16 includes handle 72, closure tube 50 and end effector 57, which, in the embodiment of the invention illustrated in FIG. 4, is a bipolar cutter/stapler. Alternate bipolar end effectors may include: a bipolar forceps such as the forceps illustrated in U.S. Pat. No. 5,540,684 a bipolar cutting an coagulation instrument such as the tissue cutting forceps illustrated in U.S. Pat. No. 5,445,638; a bipolar scissors such as the shears illustrated in U.S. Pat. No. 5,352,222; or a bipolar probe such as the probe illustrated in U.S. Pat. No. 5,342,357. U.S. Pat. Nos. 5,540,684 5,445,638, 5,352,222 and 5,342,357 are hereby incorporated herein by reference. Closure tube 50 is elongated to facilitate insertion of end effector 57 through a trocar cannula, thus facilitating the use of inductive electrosurgical instrument 16 in endoscopic or laparoscopic surgical procedures. Closure tube 50 may be any appropriate shape, including, for example, an elongated square or triangular tube. Handle 72, which is located at the proximal end of inductive electrosurgical instrument 16, includes grasping trigger 74, firing trigger 76 and release trigger 78. Closure tube 50, which connects handle 72 to end effector 57, includes rotation knob 70. End effector 57, which is located at the distal end of closure tube 50 includes anvil 58, cartridge channel 88 and staple cartridge 68. Inductive electrosurgical instrument 16 is similar in structure and operation to the bipolar endoscopic electrocautery linear cutting and stapling instrument illustrated and described in U.S. Pat. No. 5,403,312, which has been previously incorporated herein by reference. However inductive electrosurgical instrument 16 is cordless and electrosurgical energy is inductively coupled into electrosurgical instrument 16. In inductive electrosurgical instrument 16, electrosurgical energy is supplied to end effector 57 through one or more inductor coils which may be located in, for example, closure tube 50.

Figure 5:
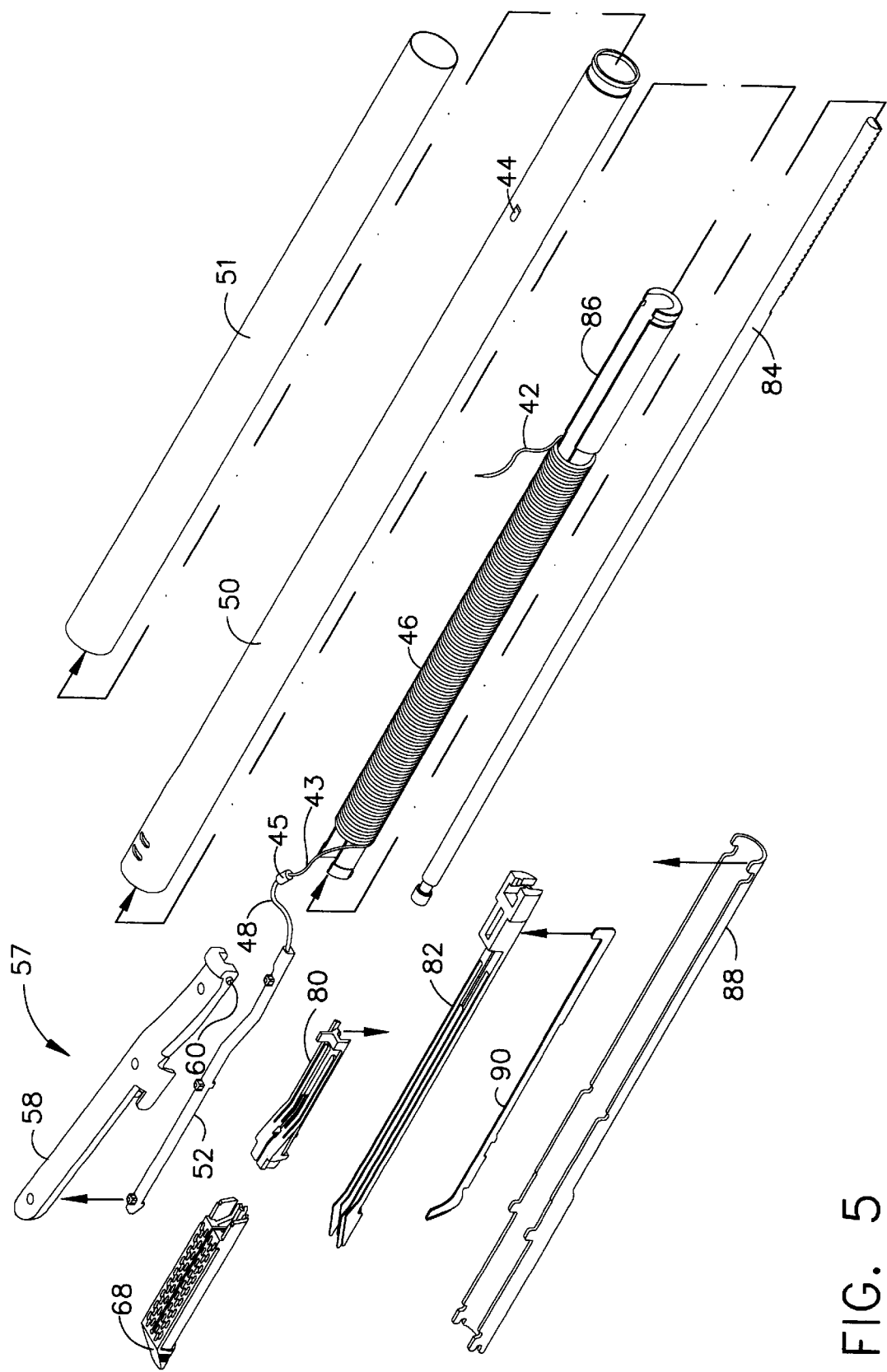
FIG. 5 is an exploded perspective view of the distal end of a cordless inductive electrosurgical instrument according to the present invention.

FIG. 5 is an exploded perspective view of the distal end of an electrosurgical instrument according to the present invention, such as electrosurgical instrument 16. In FIG. 5, outer tube 51 may be positioned over closure tube 50. In the instruments illustrated in FIG. 5, closure tube 50 is electrically conductive and outer tube 51 is constructed of an electrically insulating material. Closure tube connector 44 of closure tube 50 is electrically connected to instrument proximal inductor lead 42, which is electrically connected to the proximal end of instrument inductor coil 46. The distal end of instrument inductor 46 is electrically connected to electrical conductor 48 through instrument distal connector 45. In the embodiment of FIG. 5, electrical conductor 48 electrically couples instrument coil 46 to electrode assembly 52, which is positioned on anvil 58. Electrically conductive closure tube 50, in turn, electrically couples the proximal end of instrument coil 46 to cartridge channel 88 which, in the embodiment of the invention illustrated in FIGS. 4 and 5 is electrically conductive and acts as a return electrode. In an alternate electrosurgical instrument, instrument proximal inductor lead 42 could be connected to a second electrode on end effector 57 by an insulated wire which runs through closure tube 50 and, in such an instrument, closure tube 50 may be constructed of an insulating material. Electrode assembly 52 is positioned in anvil 58. Electrode assembly 52 may be electrically insulated from anvil 58 and closure tube 50 to prevent electrode assembly 52 from shorting to anvil 58 or closure tube 50. Conductor 48, instrument inductor coil 46, instrument proximal inductor lead 42, instrument distal inductor lead 43 and instrument distal connector 45 may also be insulated to prevent them from shorting to closure tube 50 or any of the mechanisms in closure tube 50.

Figure 6:
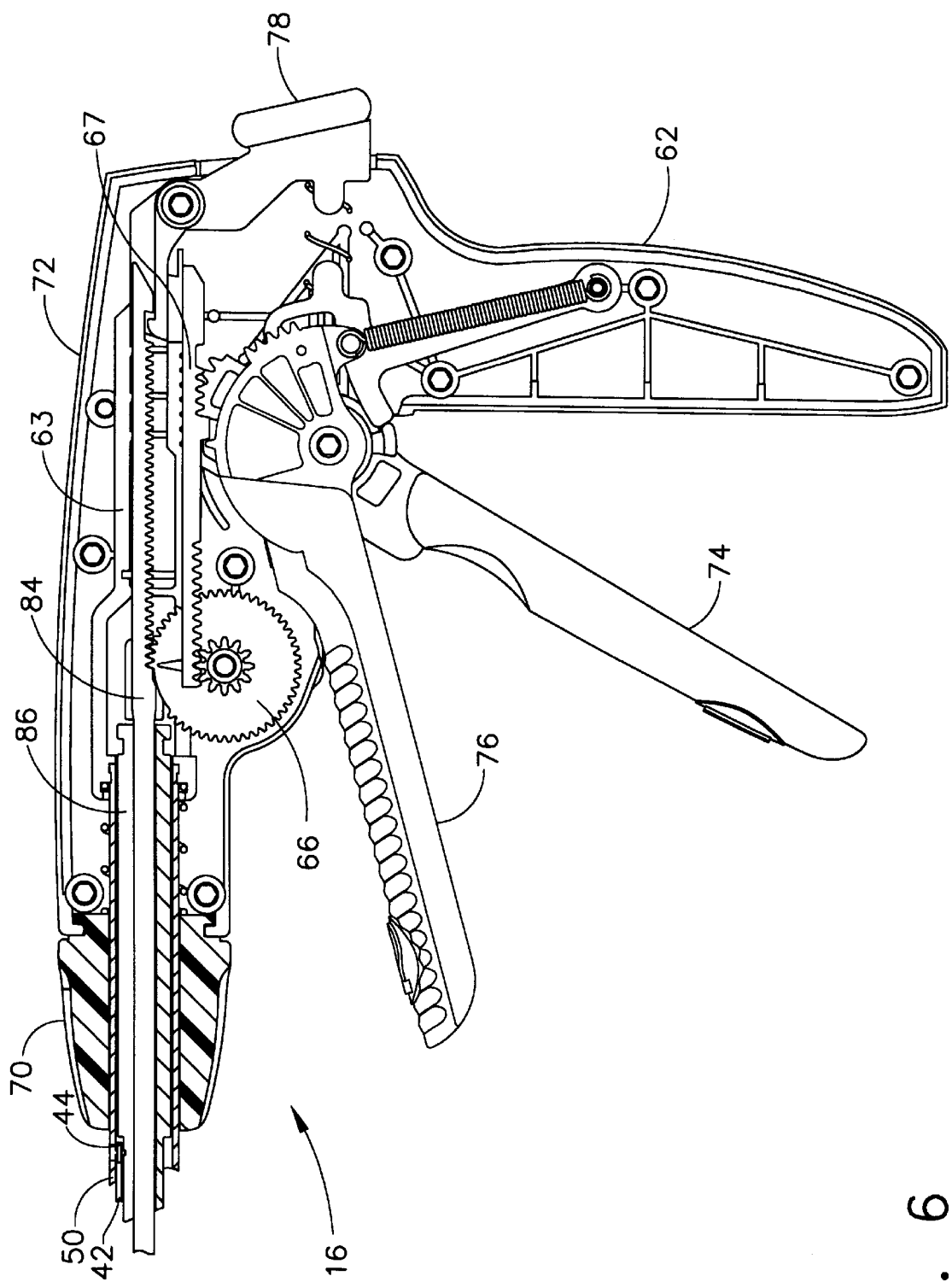
FIG. 6 is a cut away view of the handle portion of the electrosurgical instrument illustrated in FIG. 4.

FIG. 6 is a cut away view of the handle of electrosurgical instrument 16 which is illustrated in FIG. 4. In FIG. 6, handle 72 includes grip 62, grasping trigger 74 and firing trigger 76. Pivotal movement of grasping trigger 74 results in distal movement of yoke 63 and closure tube 50, closing anvil 58 against staple cartridge 68. Staple cartridge 68 is positioned in cartridge channel 88. Pivotal movement of grasping trigger 74 further releases firing rod 84 and positions firing trigger 76 to engage drive member 67. Further pivotal movement of firing trigger 76 toward grip 62 results in distal movement of drive member 67 which rotates multiplier 66 in a counterclockwise direction. Counterclockwise rotation of multiplier 66 results in distal movement of firing rod 84 which, in the embodiment of the invention illustrated herein, fires the staples in staple cartridge 68.

FIG. 7A is a cutaway view of end effector 57 of inductive cordless electrosurgical instrument 16. FIG. 7B is a cutaway view of a central portion of closure tube 50 of inductive cordless electrosurgical instrument 16. FIG. 7C is a cutaway view of a proximal portion of the of the closure tube of inductive electrosurgical instrument 16. In the embodiments of electrosurgical instrument 16 illustrated in FIGS. 7A–7C, anvil base 73 of Anvil 58 supports electrode assembly 52 and includes anvil guide 65 and staple forming slots (not shown). Electrode assembly 52 is electrically coupled to electrical conductor 48 and to anvil electrodes 55. Anvil base 73 is insulated from electrode assembly 52 by anvil insulator 59. Electrical conductor 48 is electrically connected to instrument inductor coil 46 by instrument distal connector 45 and instrument distal inductor lead 43. Instrument inductor coil 46 is positioned in the central portion of closure tube 50. Cartridge channel 88 of end effector 57 supports staple cartridge 68, wedge guide 80 and wedge block assembly 82. Cartridge channel 88 extends into and, being constructed of electrically conductive material in the embodiment illustrated in FIG. 7, is electrically coupled to electrically conductive closure tube 50. Closure tube 50 is electrically coupled to the proximal end of instrument inductor coil 46 by closure tube connector 44 and instrument proximal inductor lead 42. Thus, cartridge channel 88 may provide a return path for electrical energy coupled to anvil electrodes 55 of end effector 57 when end effector 57 is used to grasp tissue or other electrically conductive material which touches both cartridge channel 88 and anvil electrodes 55. Electrosurgical energy coupled to cartridge channel 88 may be coupled back to electrosurgical trocar 11 through instrument inductor coil 46. Closure tube 50 may be electrically insulated from surrounding structures or tissue by, for example, covering closure tube 50 with a sleeve of electrically insulating material 51. Closure tube 50 also supports and encloses the proximal end of anvil 58, the proximal end of cartridge channel 88, firing rod 84, the proximal end of knife 90, channel retainer 86 and at least a portion of wedge block assembly 82 and wedge guide 80. Closure tube 50 may also be constructed of a ferromagnetic material such as, for example, iron, to facilitate magneting coupling between inductor coil 91 in inductive electrosurgical trocar 11 and instrument inductor coil 46 in inductive electrosurgical instrument 16. Anvil 58 opens and closes by, for example, pivoting around one or more pivot pins 60.

In the cordless electrosurgical instruments illustrated in FIGS. 4–7, knife 90 is connected to wedge assembly 82 and wedge assembly 82 is connected to firing rod 84, which, in turn, is operatively connected to firing trigger 76. Closure tube 50 is operatively connected to rotation knob 70, grasping trigger 74 and release trigger 78. Wedge guide 80 is fitted over wedge block assembly 82 to guide wedge block assembly 82 as firing rod 84 moves wedge block assembly 82. The structure and operation of the mechanical features of inductive electrosurgical instrument 16 may be better understood with reference to the mechanical cutting and stapling instrument illustrated and described in U.S. Pat. No. 5,597,107 which is hereby incorporated herein by reference.

Figure 8:
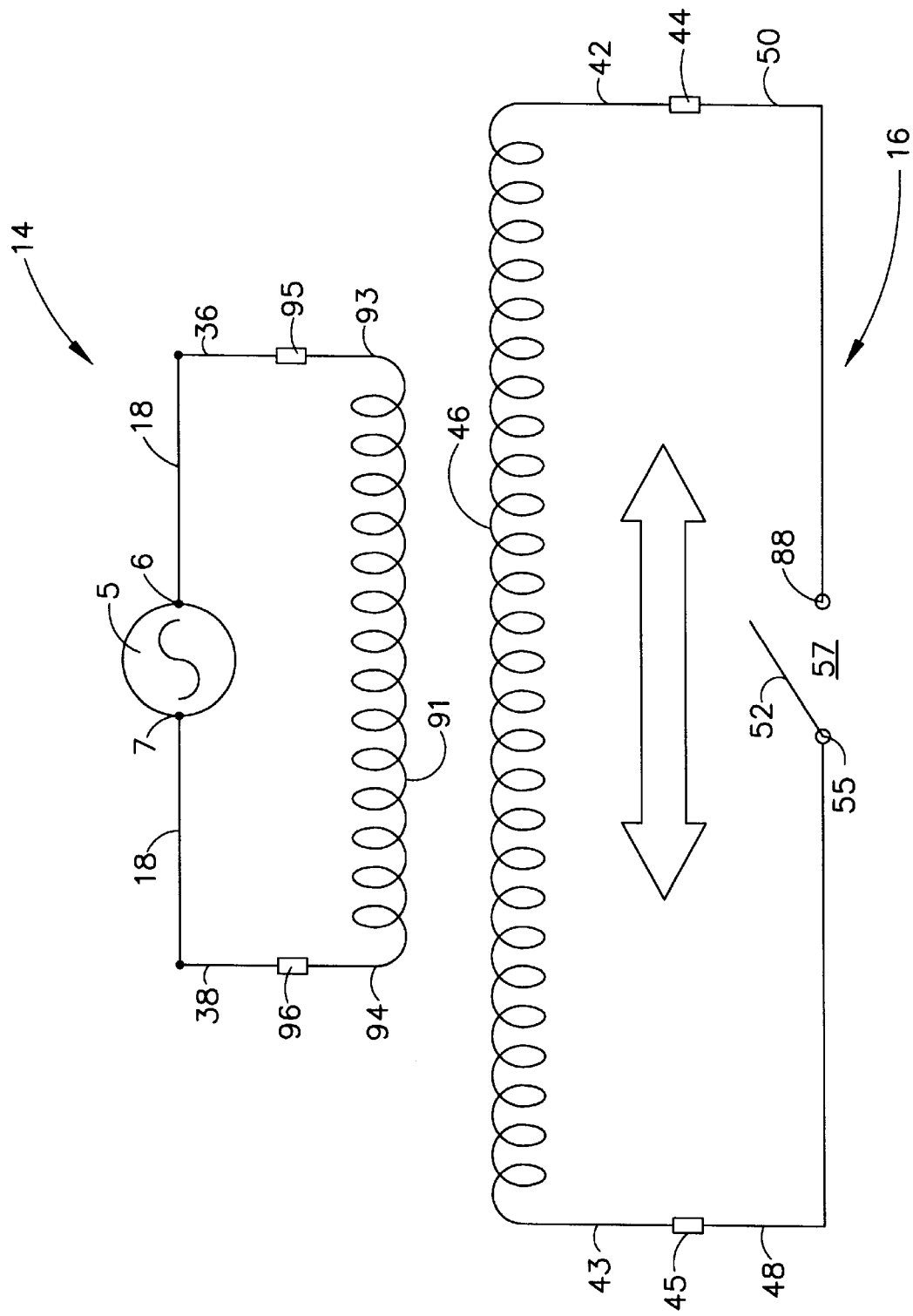
FIG. 8 is a schematic diagram graphically illustrating the inductive coupling between an inductive electrosurgical trocar or trocar adapter and an inductive electrosurgical instrument according to the present invention.

FIG. 8 is a schematic diagram graphically illustrating the inductive coupling between inductive electrosurgical adapter 14 of inductive electrosurgical trocar 11 and inductive electrosurgical instrument 16. In FIG. 8, first output 6 of electrosurgical generator 5 is electrically connected to a first end of inductor coil 91 through electric cord 18, upper conductor 36, proximal connector 95 and proximal inductor lead 93. Upper conductor 36 is electrically connected to electric cord 18. Second output 7 of electrosurgical generator 5 is electrically connected to a second end of inductor coil 91 through electric cord 18, lower conductor 38, distal connector 96 and distal inductor lead 94. Lower conductor 38 is electrically connected to electric cord 18. When end effector 57 is closed around electrically conductive material such as biological tissue which is also in contact with cartridge channel 88, the electrical circuit from instrument proximal inductor lead 42 of instrument inductor coil 46 to instrument distal inductor lead 43 of instrument inductor coil 46 is completed through closure tube connector 44, electrically conductive closure tube 50, cartridge channel 88, the conductive material being grasped, anvil electrodes 55 of electrode assembly 52, electrical conductor 48, instrument distal connector 45 and instrument distal inductor lead 43. Thus, with end effector 57 closed around conductive material and electrosurgical generator 5 turned on, electrosurgical energy, such as electrical current at a suitable output frequency and power, passes from electrosurgical generator 5, through inductor coil 91 (which is electromagnetically coupled to instrument inductor coil 46) through instrument inductor coil 46, to end effector 57 and returns through instrument inductor coil 46 and inductor coil 91 back to electrosurgical generator 5.

As FIG. 8 schematically illustrates, instrument inductor coil 46 is elongated so that movement of inductive electrosurgical instrument 16 in central aperture 19 does not result in loss of electromagnetic coupling between inductor coil 91 and instrument inductor coil 46. Thus, even as inductive electrosurgical instrument 16 is moved within inductive electrosurgical trocar 11 to facilitate treatment of the patient, inductive coupling between inductor coil 91 and instrument inductor coil 46 may be maintained. It may also be advisable, in certain situations, to include one or more matching capacitors (not shown) in either inductive electrosurgical trocar 11 or in inductive electrosurgical instrument 16 to electrically match inductive electrosurgical instrument 16 to inductive electrosurgical trocar 11 in order to increase the power coupled to tissue grasped by end effector 57. In particular, such a matching capacitor(s) (not shown) would be selected to make the load represented by the trocar, instrument and tissue appear to be substantially resistive at the frequency of interest (e.g. the frequency at which the electrosurgical energy is being transmitted to the tissue).

In operation, trocar cannula 8 is used with a conventional trocar orbitor (not shown) to penetrate the wall of a body cavity such as, for example, the abdominal wall of a human being. After the body wall is penetrated, the obturator assembly is withdrawn from trocar cannula 8, and the cannula is used as an access portal for the passage of various endoscopic instruments to provide, for example, access to the internal organs of a human being. Where the endoscopic instrument to be used is a cordless inductive electrosurgical instrument such as electrosurgical instrument 16, inductive electrosurgical adapter 14 may be attached to cannula housing 12 of trocar cannula 8 using, for example, locking connector 17. Once inductive electrosurgical adapter 14 is attached to trocar cannula 8 and electric cord 18 is attached to a suitable electrosurgical generator (such as generator 5 in FIG. 8), inductive electrosurgical trocar 11 may be used to provide electrosurgical energy to cordless inductive electrosurgical instruments such as electrosurgical instrument 16. When a cordless inductive electrosurgical instrument such as electrosurgical instrument 16, is inserted into a body cavity through, for example, inductive electrosurgical trocar 11, end effector 57 passes through trocar cannula 8 and into the body cavity while most of closure tube 50 remains in the trocar. Handle 72, which is outside of inductive electrosurgical trocar 11, may be manipulated by the surgeon to control the position of end effector 57.

A cordless inductive bipolar electrosurgical instrument according to the present invention, such as electrosurgical instrument 16 of FIG. 7 may be used by inserting the cordless instrument into an appropriate inductive electrosurgical trocar such as the electrosurgical trocar illustrated in FIG. 1. In the inductive electrosurgical trocar illustrated in FIG. 1, electrosurgical energy is provided to instrument 16 by, for example, inductive electromagnetic coupling between inductor coil 91 of inductive electrosurgical trocar 11 and instrument inductor coil 46 of inductive electrosurgical instrument 16. The diameter of central aperture 19 generally corresponds with the outer diameter of closure tube 50 so that closure tube 50 slides through central aperture 19 and the interior of cannula tube 10. Efficient electromagnetic coupling should be maintained so long as at least a portion of instrument inductor coil 46 is positioned in central aperture 19 opposite at least a portion of inductor coil 91. At least one of closure tube 50 and interior wall 92, may be preferably formed of a ferromagnetic material, or any suitable material having a high relative magnetic permeability, to facilitate and enhance electromagnetic coupling between inductive coil 91 and instrument inductor coil 46. As indicated previously, a compression member (not shown) may be used to help to ensure that interior wall 92 and closure tube 50 maintain good physical contact, minimizing any air gap and enhancing inductive coupling between the inductor coil 91 and instrument inductor coil 46. Electromagnetic coupling may also be enhanced by using multiple inductors or multiple coil layers in inductive electrosurgical trocar 11 or in inductive electrosurgical instrument 16. With instrument inductor coil 46 positioned opposite inductor coils 91, electrosurgical energy may be supplied to inductive electrosurgical instrument 16 through electric cord 18 and inductive electrosurgical trocar 11. In the embodiments of the invention illustrated herein, electrosurgical energy supplied to trocar 11 by electric cord 18 passes through conductors 36 and 38 to inductor leads 93 and 94 and into inductive electrosurgical instrument 16 via electromagnetic coupling between inductor coils 91 and instrument inductor coil 46. Electrosurgical energy supplied to inductive electrosurgical instrument 16 by electromagnetic coupling between coils 91 and 46 may be supplied to end effector 57 via the circuit formed by instrument distal inductor lead 43, instrument distal connector 45, electrical conductor 48, electrode assembly 52, cartridge channel 88, closure tube 50, closure tube connector 44 and instrument proximal inductor lead 42. This circuit is completed when biological tissue or other conductive material is grasped by end effector 57, providing an electrical path from electrode assembly 52 to cartridge channel 88. In the embodiment of inductive electrosurgical instrument 16 illustrated and described herein, cartridge channel 88 and anvil electrodes 55 are electrically conductive. Thus, where electrode assembly 52 acts as a primary electrode, cartridge channel 88 acts as a secondary or return electrode. When electrically conductive tissue is grasped by end effector 57 and an electrosurgical generator is connected to inductor coil 91 and inductive electrosurgical instrument 16 is positioned in inductive electrosurgical trocar 11 as described herein, electrosurgical energy will flow through the grasped tissue coagulating or otherwise electrosurgically treating the grasped tissue. It may also be advantageous to provide one or more switches (not shown) to control the flow of electrosurgical energy to trocar 11 or to end effector 57 of inductive electrosurgical instrument 16.

While preferred embodiments of the present invention have been shown and described herein, it will be obvious to those skilled in the art that such embodiments are provided by way of example only. Numerous variations, changes, and substitutions will now occur to those skilled in the art without departing from the invention. Accordingly, it is intended that the invention be limited only by the spirit and scope of the appended claims.

What is claimed is:

1. An electrosurgical instrument wherein said electrosurgical instrument comprises:
   a) a handle;
   b) an end effector operatively connected to said handle;
   c) an elongated tube connecting said end effector to said handle;
   d) an inductor positioned in said elongated tube, wherein said inductor comprises an inductive coil including first and second electrical leads, said first and second electrical leads being electrically coupled directly to said end effector.

2. An electrosurgical instrument according to claim 1 wherein said elongated tube includes a ferromagnetic material.

3. An electrosurgical instrument according to claim 1 wherein said elongated tube includes a material having a high relative magnetic permeability.

4. An endoscopic electrosurgical instrument wherein said electrosurgical instrument comprises:
   a) a handle;
   b) an end effector operatively connected to said handle and including a first electrode and a second electrode;
   c) an elongated tube connecting said end effector to said handle;
   d) an inductor positioned in said elongated tube, wherein said inductor is electrically connected directly to said first electrode by a first electrical conductors, and directly to said second electrode by a second electrical conductor.

5. An electrosurgical instrument according to claim 4 wherein said elongated tube includes a ferromagnetic material.

6. An electrosurgical instrument according to claim 4 wherein said elongated tube includes a material having a high relative magnetic permeability.

7. An electrosurgical instrument wherein said electrosurgical instrument comprises:
   a) a handle including an actuator;
   b) an end effector including first and second electrodes wherein said end effector comprises a first grasping element and a second grasping element;
   c) an elongated, electrically conductive tube having an internal surface and an external surface, wherein said tube connects said end effector to said handle and includes a mechanism operatively connecting said end effector to said actuator;
   d) an inductor coil positioned in said tube around said mechanism and extending along a central axis of said tube;
   e) first and second conductors electrically connected to first and second ends of said inductor coil;
   f) said first conductor being electrically connected to said elongated tube wherein said elongated tube is electrically connected to said first electrode;
   g) said second conductor being connected to said second electrical contact.

8. An electrosurgical instrument according to claim 7 wherein said elongated tube includes a ferromagnetic material.

9. An electrosurgical instrument according to claim 7 wherein said elongated tube includes a material having a high relative magnetic permeability.

10. An inductive electrosurgical instrument wherein said electrosurgical instrument comprises:
    a) a handle means for holding said instrument;
    b) an end effector means for treating tissue wherein said end effector means is operatively connected to said handle;
    c) an elongated tube means for connecting said end effector means to said handle means;
    d) an inductive coupling means for electrically coupling electricity through said elongated tube means to said instrument, wherein said inductive coupling means is electrically connected directly to said end effector by first and second conductors.

11. An electrosurgical instrument according to claim 10 wherein said elongated tube includes a ferromagnetic material.

12. An electrosurgical instrument according to claim 10 wherein said elongated tube includes a material having a high relative magnetic permeability.

13. An endoscopic inductive electrosurgical instrument wherein said electrosurgical instrument comprises:
    a) a handle means for holding said instrument;
    b) an end effector means for treating tissue wherein said end effector means is operatively connected to said handle means and including first and second electrode means for transmitting electrical energy to tissue contacted by said end effector;
    c) an elongated tube for connecting said end effector to said handle;
    d) an inductive coupling means for coupling electrical energy to said first electrode wherein said inductive coupling means is positioned in said elongated tube; and
    e) first and second electrical conductor means for conducting electricity from said inductive coupling means directly to said electrode means.

14. An electrosurgical instrument according to claim 13 wherein said elongated tube includes a ferromagnetic material.

15. An electrosurgical instrument according to claim 13 wherein said elongated tube includes a material having a high relative magnetic permeability.

16. An electrosurgical instrument wherein said electrosurgical instrument comprises:
    a) a handle means for holding said instrument;
    b) an actuator means attached to said handle for opening and closing an end effector
    c) an end effector means for manipulating tissue, said end effector means including first and second electrodes;

d) an elongated, electrically conductive tube means for operatively connecting said handle to said end effector, including a mechanism means for operatively connecting said end effector to said actual;

e) first and second electric conductor means for electrically connecting said inductor means directly to said end effector.

17. An electrosurgical instrument according to claim 16 wherein said elongated tube means includes a ferromagnetic material.

18. An electrosurgical instrument according to claim 16 wherein said elongated tube means includes a material having a high relative magnetic permeability.

* * * * *